US010758633B2

(12) United States Patent
Wei et al.

(10) Patent No.: US 10,758,633 B2
(45) Date of Patent: Sep. 1, 2020

(54) NANOPARTICLES FOR MAGNETIC RESONANCE IMAGING APPLICATIONS

(71) Applicant: Massachusetts Institute of Technology, Cambridge, MA (US)

(72) Inventors: He Wei, Cambridge, MA (US); Oliver T. Bruns, Boston, MA (US); Ou Chen, Mansfield, MA (US); Moungi G. Bawendi, Cambridge, MA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 0 days.

(21) Appl. No.: 16/149,082

(22) Filed: Oct. 1, 2018

(65) Prior Publication Data

US 2019/0022258 A1    Jan. 24, 2019

Related U.S. Application Data

(62) Division of application No. 14/852,432, filed on Sep. 11, 2015, now Pat. No. 10,086,094.

(60) Provisional application No. 62/050,477, filed on Sep. 15, 2014.

(51) Int. Cl.
     *A61K 9/00*         (2006.01)
     *A61K 49/18*       (2006.01)
     *H01F 1/00*        (2006.01)

(52) U.S. Cl.
     CPC ....... *A61K 49/1839* (2013.01); *H01F 1/0054* (2013.01)

(58) Field of Classification Search
     CPC ................................. A61K 49/1839
     See application file for complete search history.

(56) References Cited

U.S. PATENT DOCUMENTS

| | | | |
|---|---|---|---|
| 8,574,549 B2 | 11/2013 | Butts et al. | |
| 9,078,920 B2 | 7/2015 | Bawendi et al. | |
| 2010/0166666 A1 | 7/2010 | Butts et al. | |
| 2012/0195835 A1 | 8/2012 | Woo et al. | |
| 2013/0184444 A1 | 7/2013 | Bawendi et al. | |

FOREIGN PATENT DOCUMENTS

| | | |
|---|---|---|
| JP | 2013-534893 | 9/2013 |
| WO | 2012018240 | 2/2012 |
| WO | 2013090601 | 6/2013 |

OTHER PUBLICATIONS

Wei, Compact Zwitterion-Coated Iron Oxide Nanoparticles for Biological Applications, Nano Letters, 2012, 12, 22-25.
International Search Report and Written Opinion for PCT/US2015/049524 dated Mar. 3, 2016.
Byung Hyo Kim et al: "Large-Scale Synthesis of Uniform and Extremely Small-Sized Iron Oxide Nanoparticles for High-Resolution I 1 Magnetic Resonance Imaging Contrast Agents", Journal of the American Chemical Society vol. 133, No. 32, Aug. 17, 2011 (Aug. 17, 2011), pp. 12624-12631.
Office action mailed in European Application 15778408.3 dated Jan. 7, 2020.

*Primary Examiner* — Paul W Dickinson
(74) *Attorney, Agent, or Firm* — Steptoe & Johnson LLP

(57) ABSTRACT

A method of preparing a coated nanoparticle can include decomposing a compound to produce a nanoparticle, oxidizing the nanoparticle to produce an oxidized nanoparticle, and coating the oxidized nanoparticle with a zwitterionic ligand to produce the coated nanoparticle. The coated nanoparticle or the nanoparticle can be used in magnetic resonance imaging.

4 Claims, 7 Drawing Sheets

| | Field Strength (T) | Core (nm) | HD (nm) | $r_1$ ($s^{-1}mM^{-1}$) | $r_2$ ($s^{-1}mM^{-1}$) | $r_2/r_1$ |
|---|---|---|---|---|---|---|
| Feraheme® | 7 | 3-10 | 16 | 3.1 | 68 | 22 |
| ZDS-coated Fe$_3$O$_4$ NPs | 7 | 7 | 12 | 3.4 | 60 | 18 |
| ZDS-coated Fe$_3$O$_4$ NPs | 7 | 5.5 | 9 | 2.9 | 51 | 18 |
| ZDS-coated Fe$_3$O$_4$ NPs | 7 | 3.5 | 6 | 2.0 | 32 | 16 |
| ZDS-coated Fe$_3$O$_4$ NPs | 7 | 3 | 5 | 1.5 | 17 | 11 |
| ZDS-coated Fe$_3$O$_4$ NPs | 0.5 | 3 | 5 | 2.4 | 3.7 | 1.5 |

FIG. 2

NANOPARTICLES FOR MAGNETIC RESONANCE IMAGING APPLICATIONS

CLAIM OF PRIORITY

This application is a divisional of U.S. application Ser. No. 14/852,432, filed Sep. 11, 2015, now U.S. Pat. No. 10,086,094, which claims priority to U.S. Provisional Application No. 62/050,477, filed on Sep. 15, 2014, each of which is incorporated by reference in its entirety.

FEDERAL SUPPORT

This invention was made with Government support under Grant Nos. R01 CA126642 and U54 CA151884 awarded by the National Institutes of Health and under Grant No. CHE-0714189 awarded by the National Science Foundation and under Contract No. W911NF-13-D-0001 awarded by the Army Research Office. The Government has certain rights in the invention.

FIELD OF THE INVENTION

The invention relates to nanoparticles for imaging applications.

BACKGROUND

Nanometer sized particles often exhibit interesting electrical, optical, magnetic, and chemical properties, which cannot be achieved by their bulk counterparts. Magnetic nanoparticles can find applications in magnetic memory devices, ferrofluids, refrigeration systems, medical imaging, drug targeting, and catalysis. Magnetic oxide nanoparticles can be synthesized by using micro emulsion and other methods.

SUMMARY

In one aspect, a method of preparing a coated nanoparticle can include decomposing a compound in a solvent including an acid to produce a nanoparticle, oxidizing the nanoparticle with a reagent to produce an oxidized nanoparticle, and coating the oxidized nanoparticle with a zwitterionic ligand to produce the coated nanoparticle.

In certain embodiments, the coated nanoparticle can be magnetic.

In certain embodiments, the acid can include an oleic acid. The acid can include a stearic acid. The solvent can include a 1-hexadecene, a 1-octadecene, a 1-eicosene, a 1-dococene, or a 1-tetracosane, or a mixture thereof.

In certain embodiments, the compound can include an iron oleate. The coated nanoparticle can include an iron oxide. The reagent can include an alkyl amine oxide. A hydrodynamic diameter of the coated nanoparticle can be between 5 nm and 10 nm. Size is a diameter of the nanoparticle.

In certain embodiments, the coated nanoparticle can have a size of between 2.5 nm and 3 nm. An inorganic core of the coated nanoparticle can have a size of between 2.5 nm and 7 nm. The coated nanoparticle can have a hydrodynamic diameter of less than 5 nm.

In certain embodiments, the zwitterionic ligand can include a zwitterionic dopamine sulfonate ligand. The zwitterionic ligand can be switched to a dopamine sulfonate ligand.

In another aspect, a T1 contrast agent for magnetic resonance imaging or magnetic resonance angiography can include a nanoparticle, wherein an inorganic core of the nanoparticle can have a size of between 2.5 and 4 nm, wherein the nanoparticle can have a hydrodynamic diameter of less than 5 nm, and wherein the nanoparticle can be magnetic.

In certain embodiments, the inorganic core can have a size of between 2.5 and 3.5 nm. A surface of the nanoparticle can include a zwitterionic dopamine sulfonate ligand. A surface of the nanoparticle can include a dopamine sulfonate ("DS") ligand. The nanoparticle can include an iron oxide.

In another aspect, a method for magnetic resonance imaging or magnetic resonance angiography can include introducing a T1 contrast agent comprising a nanoparticle into a subject, wherein an inorganic core of the nanoparticle has a size of between 2.5 and 4 nm, wherein the nanoparticle has a hydrodynamic diameter of less than 5 nm, and wherein the nanoparticle is magnetic; and creating an imaging signal of the subject. In certain embodiments, the inorganic core of the nanoparticle can have a size of between 2.5 and 3.5 nm. A surface of the nanoparticle can include a zwitterionic dopamine sulfonate ligand. A surface of the nanoparticle can include a DS ligand. The nanoparticle can include an iron oxide.

Other aspects, embodiments, and features will be apparent from the following description, the drawings, and the claims.

BRIEF DESCRIPTION OF THE DRAWINGS

FIG. 2 shows $r_1$ and $r_2$ relaxivity measurements of a series of iron oxide NPs.

DETAILED DESCRIPTION

Figure 1A:
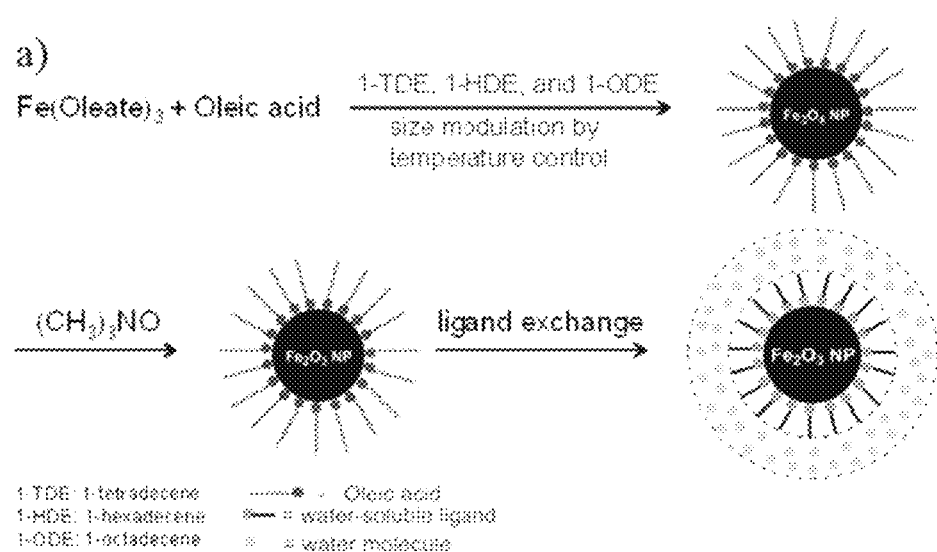
FIG. 1(A) shows a synthetic route of a series of sizes of monodisperse iron oxide nanoparticles ("NPs")
Figures 1B, 1C, 1D, 1E:
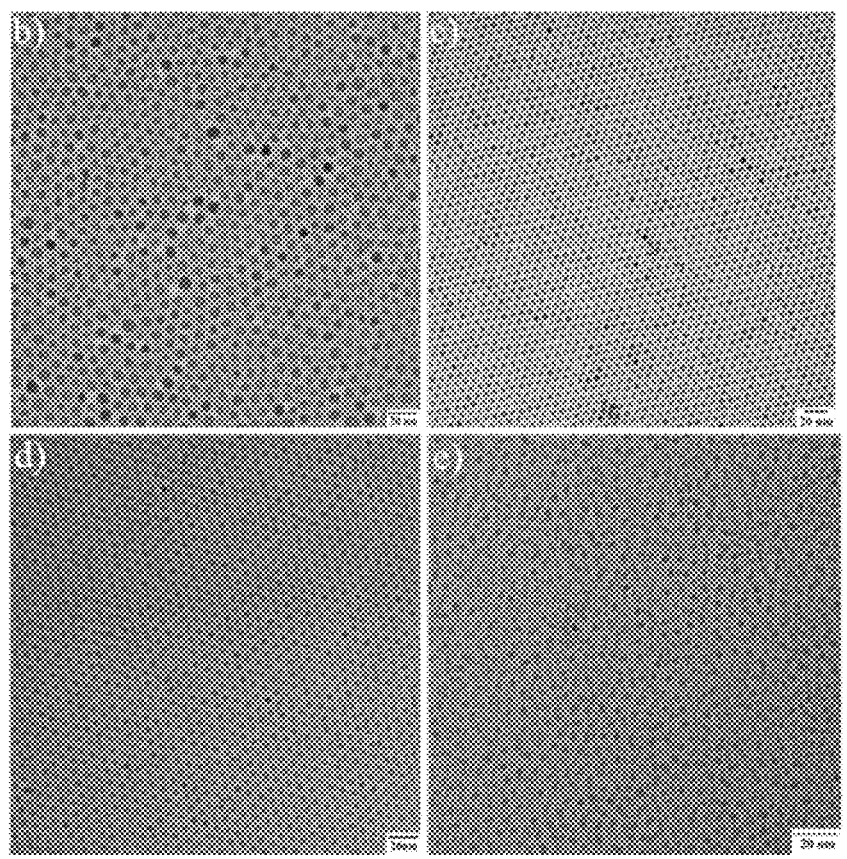
FIG. 1(B)-(E) show HR TEM images of iron oxide NPs with 7.0, 5.5, 3.0, and 2.5 nm inorganic core diameter, respectively.

Magnetic resonance imaging (MRI) has played an important role in clinical imaging and diagnosis since its development in 1980s and it has recently served as an excellent tool in the biomedical research domains. See, for example, Gore, J. C. et al., *Magnetic Resonance Imaging* 2011, 29, 587, which is incorporated by reference in its entirety. After 30 years of rapid and steady progress, $T_1$ and $T_2$ weighted MRI techniques nowadays possess the advantages of high spatial resolution, significant tissue and cellular contrast, in situ visualization of the functions of organs (e. g., brain) in living animals, as well as three-dimensional and non-invasive detection ability. See, for example, Na, H. B.; Song, I. C.; Hyeon, T. *Adv. Mater.* 2009, 21, 2133-2148; Zhu, D. R.; Liu, F. Y.; Ma, L. N.; Liu, D. J.; Wang, Z. X. *International Journal of Molecular Sciences* 2013, 14, 10591, each of which is incorporated by reference in its entirety. More recently, the $T_1$ weighted MRI research and applications has been very promising, for the reason that the $T_1$ contrast agents demonstrate bright signals that can be exempted from bleeding or metal deposition and $T_1$ weighted MRI generally shows higher spatial resolutions by reducing the artifacts that are caused by breathing or air/tissue boundary in $T_2$ weighted MRI. See, for example, Kim, B. H.; Lee, N.; Kim, H.; An, K.; Park, Y. I.; Choi, Y.; Shin, K.; Lee, Y.; Kwon, S. G.; Na, H. B.; Park, J. G.; Ahn, T. Y.; Kim, Y. W.; Moon, W. K.; Choi, S. H.; Hycon, T. *Journal of the American Chemical Society* 2011, 133, 12624, which is incorporated by reference in its entirety. The uses of contrast agents, which enhance the contrasts of MRI by changing the water proton relaxation time, are essential to acquire high-contrast $T_1$ weighted MR images. See, for example, Harisinghani, M. G.; Barentsz, J.; Hahn, P. F.; Deserno, W. M.; Tabatabaei, S.; van de Kaa, C. H.; de la Rosette, J.; Weissleder, R. *New England Journal of Medicine* 2003, 348, 2491, which is incorporated by reference in its entirety.

The $r_2/r_1$ ratio is an important value for the evaluation of contrast agents, i.e. low(high) $r_2/r_1$ ratio results in good $T_1(T_2)$ weighted MR images. $r_2$ can escalate with the increase of saturation magnetization ("$M_s$") and hydrodynamic diameter ("HD"). Therefore, in order to achieve a low $r_2/r_1$ ratio for high-quality $T_1$ weighted MRI, the magnetic core needs to be small to ensure a low $M_s$ and the ligand coating shell needs to be thin for small $r_2$. Hydrophobic and hydrophilic Gd-based chelates and gadolinium oxide nanoparticles can be used as $T_1$ contrast agents in clinics and they can have high $T_1$ contrast because of their high $r_1$ and low $r_2$ (i.e. low $r_2/r_1$ ratio). However, Gd-based compounds have recently shown long-term and severe toxicity towards senior adults and patients with deficient kidney functions. See, for example, Bruns, O. T. et al., *Nature Nanotechnology* 2009, 4, 193; Penfield, J. G. et al., *Nat. Clin. Pract. Nephrol.* 2007, 3, 654, each of which is incorporated by reference in their entirety. Gadolinium has been related with nephrogenic systemic fibrosis in these cases. See, for example, Bennett, Charles L.; al., et *Clin Kidney J* 2012, 5, 82 82, which is incorporated by reference in its entirety. The high toxicity of gadolinium also made it impossible for in vivo specific targeting, where the contrast agents can remain in human body for an extended period of time. In addition to the $r_2/r_1$ ratio and non-toxicity, renal clearance is also an important property that can benefit contrast agents in clinical uses. Because the renal clearance of contrast agents would allow rapid urinary excretions, minimizing the exposure of human body to contrast agents and enabling a more efficient in vivo specific targeting as non-specific contrast agents are cleared.

NPs can be coated with hydrophobic ligands, which can be exchanged for appropriate ones that give high colloidal stability in aqueous biofluids and to avoid aggregation. The nanoparticle hydrodynamic diameter can be defined as the apparent size of a dynamic hydrated/solvated particle, and can be highly related to their capabilities for effectively overcoming the biological defense system and vascular barriers. For example, NPs with a large hydrodynamic diameter (e.g. >100 nm) can be taken up by phagocytes. Smaller NPs (e.g. 1-30 nm) can escape from phagocytes and travel through blood vessels. Small-sized NPs can have enhanced permeability and retention effects at the target tissues because they can easily pass through the larger fenestrations of the blood vessels in the vicinity of cancerous tissues.

Superparamagnetic iron oxide nanoparticles (SPIONs) are single-domain magnetic iron oxide particles with their sizes of a few nanometers to tens nanometers. See, for example, Harisinghani, M. G.; Barentsz, J.; Hahn, P. F.; Deserno, W. M.; Tabatabaei, S.; van de Kaa, C. H.; de la Rosette, J.; Weissleder, R. *New Engl. J. Med.* 2003, 348, 2491; Hyeon, T.; Lee, S. S.; Park, J.; Chung, Y.; Bin Na, H. *J. Am. Chem. Soc.* 2001, 123, 12798; Jun, Y. W.; Lee, J. H.; Cheon, *J. Angewandte Chemie-International Edition* 2008, 47, 5122, each of which is incorporated by reference in its entirety. The iron oxide magnetic nanoparticles (e.g., magnetite and maghemite) are known for their monodispersity in synthesis, superior stability to organic solvents and aqueous media, high saturation magnetic moment, and well-defined nontoxicity towards living animals. See, for example, Latham A. H.; Williams, M. E. *Accounts of Chemical Research* 2008, 41, 411, which is incorporated by reference in its entirety. As a result, iron oxide nanoparticle-based Feridex™ and Resovist™ are both clinically approved commercially available $T_2$ contrast agents and Feraheme™ is clinically approved commercially available iron supplements. Consequently, there remains a need for the development of iron oxide nanoparticle-based $T_1$ contrast agents. Polyethylene glycol (PEG) coated iron oxide nanoparticles with a 3 nm inorganic core diameter and a 15 nm HD and an $r_2/r_1$=6.1 at 3 T can be prepared. Moreover, citrate-coated superparamagnetic iron oxide nanoparticles (VSOP) with a 4 nm inorganic core diameter and a 7 nm HD and an $r_2/r_1$=2.1 at 1.5 T can be prepared. See, for example, Schnorr, J.; al, et *Cardiac Magnetic Resonance* 2012, 184, 105 105, which is incorporated by reference in its entirety. However, these iron oxide nanoparticles have HDs larger than 5.5 nm, which is the threshold for nanoparticles to be renal cleared. See, for example, Choi, H. S.; Liu, W.; Misra, P.; Tanaka, E.; Zimmer, J. P.; Kandapallil, B.; Bawendi, M. G.; Frangioni, J. V. *Nature Biotechnology* 2007, 25, 1165, which is incorporated by reference in its entirety.

Iron oxide is more biocompatible than gadolinium- or manganese based materials because the iron species are rich in human blood. An ideal T1 contrast agents should have high $r_1$ value and low $r_2/r_1$ ratio to maximize the T1 contrast effect. Although ferric ($Fe^{3+}$) ions having 5 unpaired electrons increase the $r_1$ value, the high $r_2$ of iron oxide nanoparticles derived from innate high magnetic moment prevents them from being utilized as T1 contrast agent. This problem can be resolved by decreasing size of the magnetic nanoparticles. The magnetic moment of magnetic nanoparticles rapidly decreases as their sizes decrease. The small size iron oxide nanoparticles can be used as T1 contrast agents. A T1 contrast agent for magnetic resonance imaging can include a nanoparticle, wherein the inorganic core has a size of between 2 and 4 nm, wherein the nanoparticle has a hydrodynamic diameter of less than 5 nm, and wherein the nanoparticle is magnetic.

Iron oxide nanoparticles with ultra-small inorganic diameter of 3 nm and HD of 5 nm can be prepared, endowing them with lower $r_2/r_1$ value and renal clearance property as high $T_1$ contrast agents.

A method of preparing a coated nanoparticle can include decomposing a compound in a solvent including an acid to produce a nanoparticle, oxidizing the nanoparticle with a reagent to produce an oxidized nanoparticle, and coating the oxidized nanoparticle with a zwitterionic ligand to produce the coated nanoparticle. The coated nanoparticle can include an iron oxide. The reagent can include an alkyl amine oxide, such as a trimethylamine N-oxide.

A method of preparing a nanoparticle can include decomposing a compound at a temperature of 290° C.-390° C. in a solvent, adding an acid to the solvent to form a reaction mixture, increasing the temperature of the reaction mixture to boiling point of the reaction mixture, and heating the reaction mixture at the boiling point for 60 to 120 minutes to produce the nanoparticle.

Small zwitterionic ligands for inorganic nanoparticles can provide bio-compatible nanoparticles with small HDs, a low level of non-specific interactions, and stability with respect to time, pH and salinity. In general, a ligand for a nanoparticle can include a moiety having affinity for a surface of the nanoparticle, one or more linker moieties; and two or more charged or ionizable groups that when in aqueous solution, under at least some conditions (e.g., at least some pH values), take on opposite charges. In some embodiments, the opposite charges are permanent charges. In other words, the ligand can bind to the nanoparticle and possess zwitterionic character. Preferably, the ligand can be small, such that the HD of the ligand-bound inorganic nanoparticle is not greatly increased over the diameter of the inorganic portion of the nanoparticle. In some cases, the ligand can have a molecular weight of 1,000 Da or less, 500 Da or less, 400 Da or less, 300 Da or less, or 200 Da or less.

A zwitterionic ligand can include a first charged or ionizable group. A zwitterionic ligand can include a second charged or ionizable group. When in aqueous solution, under at least some conditions (e.g., at least some pH values), the first and second charged or ionizable groups can take on opposite charges, thereby imparting zwitterionic character. Groups suitable for providing a positive charge for a zwitterionic ligand can include an amine, such as a primary amine, a secondary amine, a tertiary or quaternary amines. A group suitable for providing a negative charge can include alcohols, thiols, carboxylates, phosphates, phosphonates, sulfates, or sulfonates. In some embodiments, the group can include $—NR^2—$, $—NR^2R^3—$ (i.e., a quaternary amine), or an ionized form thereof. In some embodiments, the group can include $—OH$, $—SH$, $—CO_2H$, $—OPO_3H_2$, $—PO_3H$, $—OSO_3H$, $—SO_3H$, or an ionized form thereof.

A zwitterionic ligand can include an alkylene group; an alkenylene group; an alkynylene group; a cycloalkylene group; a cycloalkenylene group; a heterocycloalkylene group; an arylene group; or a heteroarylene group. A zwitterionic ligand can include a halo, hydroxy, cyano, nitro, amino, carboxy, carboxyalkyl, alkyl, alkoxy, cycloalkyl, heterocycloalkyl, aryl, or heteroaryl groups. A zwitterionic ligand can include one or more of $—C(O)—$, $—C(O)NR^c—$, $—O—$, $—OC(O)—$, $—OC(O)O—$, $—OC(O)NR^c—$, $—NR^cC(O)—$, $—NR^cC(O)O—$, $—NR^cC(O)NR^c—$, or $—S—$.

Methods of preparing particles include pyrolysis of reagents, such as iron oleate, injected into a hot, coordinating solvent. This permits discrete nucleation and results in the controlled growth of macroscopic quantities of nanoparticles. Preparation and manipulation of nanoparticles are described, for example, in U.S. Pat. Nos. 6,322,901 and 6,576,291, and U.S. Patent Application No. 60/550,314, each of which is incorporated by reference in its entirety. The method of manufacturing a nanoparticle is a colloidal growth process. Colloidal growth occurs by rapidly injecting an M donor and an X donor into a hot coordinating solvent. The injection produces a nucleus that can be grown in a controlled manner to form a nanoparticle. The reaction mixture can be gently heated to grow and anneal the nanoparticle. Both the average size and the size distribution of the nanoparticles in a sample are dependent on the growth temperature. The growth temperature necessary to maintain steady growth increases with increasing average crystal size. The nanoparticle is a member of a population of nanoparticles. As a result of the discrete nucleation and controlled growth, the population of nanoparticles obtained has a narrow, monodisperse distribution of diameters. The monodisperse distribution of diameters can also be referred to as a size. The process of controlled growth and annealing of the nanoparticles in the coordinating solvent that follows nucleation can also result in uniform surface derivatization and regular core structures. As the size distribution sharpens, the temperature can be raised to maintain steady growth. By adding more M donor or X donor, the growth period can be shortened.

The M donor can be an inorganic compound, an organometallic compound, or elemental metal. M is iron, cadmium, zinc, magnesium, mercury, aluminum, gallium, indium or thallium. The X donor is a compound capable of reacting with the M donor to form a material with the general formula MX. Typically, the X donor can a chalcogenide donor or a pnictide donor, such as a phosphine chalcogenide, a bis (silyl) chalcogenide, dioxygen, an ammonium salt, or a tris(silyl) pnictide. Suitable X donors include dioxygen, bis(trimethylsilyl) selenide (($TMS)_2Se$), trialkyl phosphine selenides such as (tri-n-octylphosphine) selenide (TOPSe) or (tri-n-butylphosphine) selenide (TBPSe), trialkyl phosphine tellurides such as (tri-n-octylphosphinc) telluride (TOPTe) or hex apropylphosphorustriamide telluride (HPPTTe), bis(trimethylsilyl)telluride (($TMS)_2Te$), bis(trimethylsilyl)sulfide (($TMS)_2S$), a trialkyl phosphine sulfide such as (tri-n-octylphosphine) sulfide (TOPS), an ammonium salt such as an ammonium halide (e.g., $NH_4Cl$), tris(trimethylsilyl) phosphide (($TMS)_3P$), tris(trimethylsilyl) arsenide (($TMS)_3As$), or tris(trimethylsilyl) antimonide (($TMS)_3Sb$). In certain embodiments, the M donor and the X donor can be moieties within the same molecule.

A coordinating solvent can help control the growth of the nanoparticle. The coordinating solvent is a compound having a donor lone pair that, for example, has a lone electron pair available to coordinate to a surface of the growing nanoparticle. Solvent coordination can stabilize the growing nanoparticle. Typical coordinating solvents include alkyl phosphines, alkyl phosphine oxides, alkyl phosphonic acids, or alkyl phosphinic acids, however, other coordinating solvents, such as pyridines, furans, and amines may also be suitable for the nanoparticle production. Examples of suitable coordinating solvents include pyridine, tri-n-octyl phosphine (TOP), tri-n-octyl phosphine oxide (TOPO) and tris-hydroxylpropylphosphine (tHPP). Technical grade TOPO can be used. 1-hexadecene, a 1-octadecene, a 1-eicosene, a 1-dococene, a 1-tetracosane, an oleic acid, a stearic acid, or a mixture thereof can be used.

Size distribution during the growth stage of the reaction can be estimated by monitoring the absorption line widths of the particles. Modification of the reaction temperature in response to changes in the absorption spectrum of the particles allows the maintenance of a sharp particle size distribution during growth. Reactants can be added to the nucleation solution during crystal growth to grow larger crystals. The nanoparticle has a diameter of less than 50 nm. A population of nanoparticles can have average diameters in the range of 1 nm to 35 nm. The nanoparticles can have average diameters of more than 35 nm.

The nanoparticle can be a member of a population of nanoparticles having a narrow size distribution. The nanoparticle can be a sphere, rod, disk, or other shape. The nanoparticle can include a core of a material. The nanoparticle can include a core having the formula MX, where M is cadmium, iron, gadolinium, zinc, magnesium, mercury, aluminum, gallium, indium, thallium, or mixtures thereof, and X is oxygen, sulfur, selenium, tellurium, nitrogen, phosphorus, arsenic, antimony, or mixtures thereof.

The core can have an overcoating on a surface of the core. The overcoating can be a material having a composition different from the composition of the core. The overcoat of a material on a surface of the nanoparticle can include a Group I compound, a Group IX-VI compound, Group II-VI compound, a Group II-V compound, a Group III-VI compound, a Group III-V compound, a Group IV-VI compound, a Group compound, a Group II-IV-VI compound, and a Group II-IV-V compound, for example, Cu, CoO, MnO, NiO, ZnO, ZnS, ZnSe, ZnTe, CdO, CdS, CdSe, CdTe, MgO, MgS, MgSe, MgTe, HgO, HgS, HgSe, HgTe, AlN, AlP, AlAs, AlSb, GaN, GaP, GaAs, GaSb, InN, InP, InAs, InSb, TlN, TlP, TlAs, TlSb, TlSb, PbS, PbSe, PbTe, or mixtures thereof. An overcoating process is described, for example, in U.S. Pat. No. 6,322,901. By adjusting the temperature of the reaction mixture during overcoating and monitoring the absorption spectrum of the core, over coated materials having high emission quantum efficiencies and narrow size distributions can be obtained. The overcoating can be between 1 and 10 monolayers thick.

The particle size distribution can be further refined by size selective precipitation with a poor solvent for the nanoparticles, such as methanol/butanol as described in U.S. Pat. No. 6,322,901. For example, nanoparticles can be dispersed in a solution of 10% butanol in hexane. Methanol can be added dropwise to this stirring solution until opalescence persists. Separation of supernatant and flocculate by centrifugation produces a precipitate enriched with the largest crystallites in the sample. This procedure can be repeated until no further sharpening of the optical absorption spectrum is noted. Size-selective precipitation can be carried out in a variety of solvent/nonsolvent pairs, including pyridine/hexane and chloroform/methanol. The size-selected nanoparticle population can have no more than a 15% rms deviation from mean diameter, preferably 10% rms deviation or less, and more preferably 5% rms deviation or less.

The outer surface of the nanoparticle can include compounds derived from the coordinating solvent used during the growth process. The surface can be modified by repeated exposure to an excess of a competing coordinating group. For example, a dispersion of the capped nanoparticle can be treated with a coordinating organic compound, such as pyridine, to produce crystallites which disperse readily in pyridine, methanol, and aromatics but no longer disperse in aliphatic solvents. Such a surface exchange process can be carried out with any compound capable of coordinating to or bonding with the outer surface of the nanoparticle, including, for example, phosphines, thiols, amines and phosphates. The nanoparticle can be exposed to short chain polymers which exhibit an affinity for the surface and which terminate in a moiety having an affinity for a suspension or dispersion medium. Such affinity improves the stability of the suspension and discourages flocculation of the nanoparticle. Nanoparticle coordinating compounds are described, for example, in U.S. Pat. No. 6,251,303, which is incorporated by reference in its entirety.

More specifically, the coordinating ligand can have the formula:

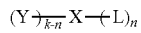

$(Y)_{k-n}X{-}(L)_n$ wherein k is 2, 3 or 5, and n is 1, 2, 3, 4 or 5 such that k-n is not less than zero; X is O, S, S=O, SO$_2$, Se, Se=O, N, N=O, P, P=O, As, or As=O; each of Y and L, independently, is aryl, heteroaryl, or a straight or branched C$_{2-12}$ hydrocarbon chain optionally containing at least one double bond, at least one triple bond, or at least one double bond and one triple bond. The hydrocarbon chain can be optionally substituted with one or more C$_{1-4}$ alkyl, C$_{2-4}$ alkenyl, C$_{2-4}$ alkynyl, alkoxy, hydroxyl, halo, amino, nitro, cyano, C$_{3-5}$ cycloalkyl, 3-5 membered heterocycloalkyl, aryl, heteroaryl, C$_{1-4}$ alkylcarbonyloxy, C$_{1-4}$ alkyloxycarbonyl, C$_{1-4}$ alkylcarbonyl, or formyl. The hydrocarbon chain can also be optionally interrupted by —O—, —S—, —N(R$^a$)—, —N(R$^a$)—C(O)—O—, —O—C(O)—N(R$^a$)—, —N(R$^a$)—C(O)—N(R$^b$)—, —O—C(O)—O—, —P(R$^a$)—, or —P(O)(R$^a$)—. Each of R$^a$ and R$^b$, independently, is hydrogen, alkyl, alkenyl, alkynyl, alkoxy, hydroxyalkyl, hydroxyl, or haloalkyl.

An aryl group is a substituted or unsubstituted cyclic aromatic group. Examples include phenyl, benzyl, naphthyl, tolyl, anthracyl, nitrophenyl, or halophenyl. A heteroaryl group is an aryl group with one or more heteroatoms in the ring, for instance furyl, pyiridyl, pyrrolyl, phenanthryl.

For a zwitterion dopamine sulfonate (ZDS) ligand, the dopamine moiety can provide strong coordination to the iron oxide surface, the sulfonate group can convey high water solubility, and the combination of a quaternary amine group and the sulfonate group can provide the ligand with a zwitterionic character, enabling pH stability and minimizing non-specific interactions with proteins.

The ZDS ligand can be synthesized from commercially available dopamine via a two step reaction: first, the sulfonation of dopamine was accomplished by ring opening of the 1,3-propane sultone, followed by methylation of the amino group by addition of iodomethane (supporting information).

ZDS, dopamine sulfonate (DS), or mixtures of ZDS with thiol-terminated catechol-derivative (TD) can replace the ligand on a surface of the nanoparticles, such as iron oxide nanoparticles.

The resulting water soluble ZDS ligand-exchanged nanoparticles (ZDS-NPs) can be stable and well dispersible at high NP concentrations in solvent, such as phosphate buffered saline (PBS). In addition, the HD of ZDS-NPs can be insensitive to pH over the pH range of 6.0-8.5, indicating good colloidal stability over physiological pHs.

The negatively charged DS-NPs can have a high non-specific affinity towards serum proteins. The negative charge from the sulfonate group on the DS ligands can electrostatically interact with some of the proteins in FBS, and electrostatic interactions are thought to be important for the binding between iron oxide NPs and bovine serum albumin. In comparison with DS-NPs, ZDS-NPs can show a reduced non-specific affinity towards serum proteins. ZDS ligands can provide good solubility and a small size to iron oxide NPs and can assure their nearly neutral overall charge, which in turn can decrease the non-specific interactions between NPs and serum proteins. Zwitterionic ZDS-NPs can be more suitable than DS-NPs for in-vivo experiments and that their overall electrically neutral (e.g. zwitterionic) nature can be important to their design.

A binary coating can be used, in which ZDS ligands can provide water-solubility and short-chain ligands can offer functionality. A short-chain ligand (TD ligand) can include a catechol, a polyalkylene glycol, and a thiol. After ligand exchange with a mixture of 85% ZDS ligand and 15% TD ligand (mol %), the resulting TD/ZDS-NPs can be conjugated by a dye and a streptavidin-maleimide (SA) via a thiol-maleimide conjugation scheme.

By using a zwitterionic dopamine sulfonate ligand coating on uperparamagnetic iron oxide nanoparticles, aqueous iron oxide nanoparticles which are water-soluble, compact, and easily functionalized can be prepared. Due to their zwitterionic nature, the ZDS-NPs can have reduced nonspecific binding to serum proteins. The functionalized iron oxide nanoparticles can be suitable for in-vivo and in-vitro applications, where antibodies, peptides, or aptamers can be conjugated to TD/ZDS-NPs for targeting and imaging, and when combined with metal-binding proteins, TD/ZDS-NPs can serve as MRI-based metal ion sensors.

Example

Small Iron Oxide Nanoparticles

Figure 3:
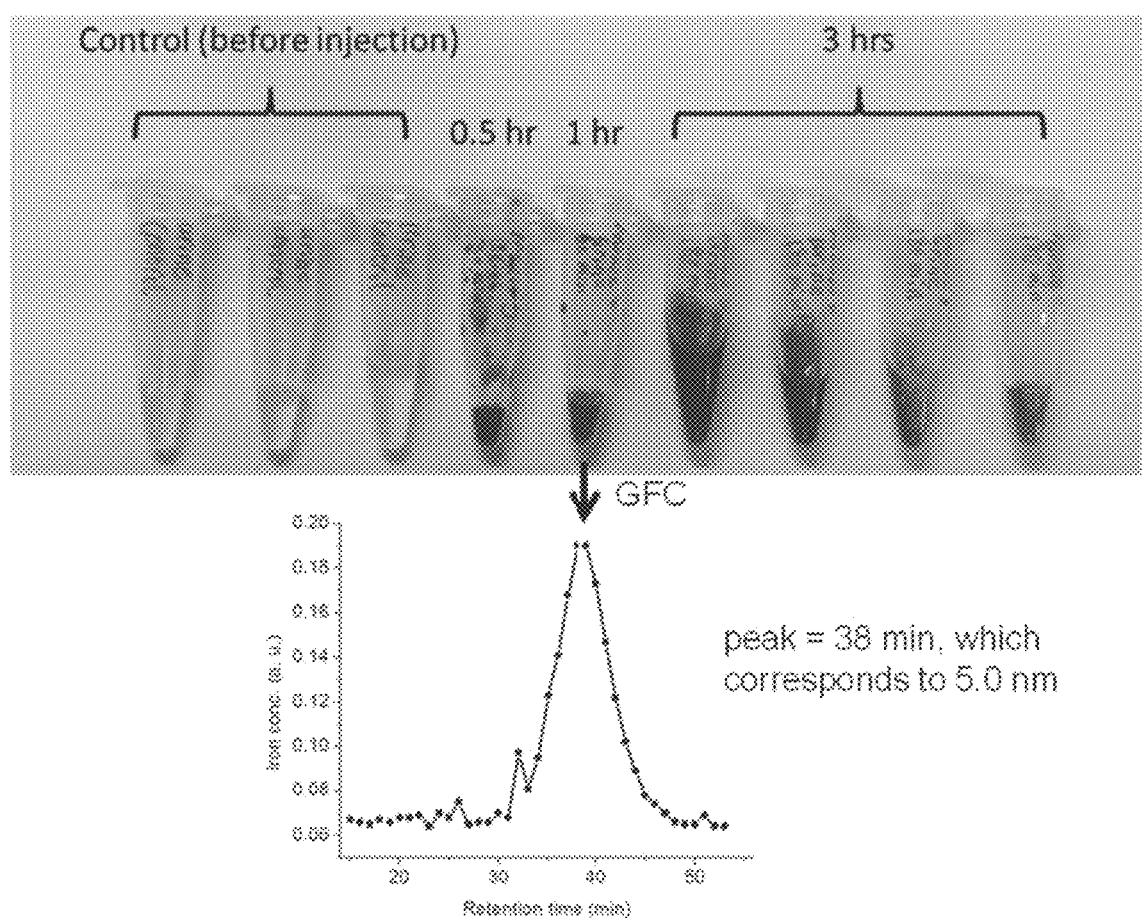
FIG. 3 is mice urine showing the renal clearance of iron oxide NPs in vivo in mice.
Figure 4:
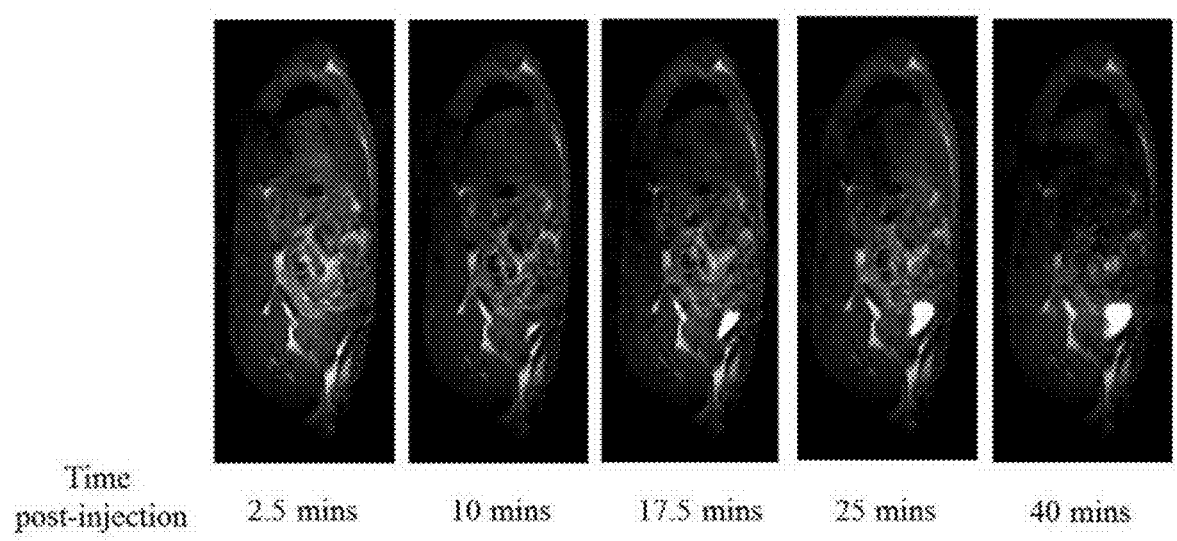
FIG. 4 shows $T_1$-weighted MRI in vivo in mice and rats.

As shown in FIG. 1a, a size series of monodisperse iron oxide nanoparticles were synthesized upon the decomposition of iron precursors (such as iron oleate or iron pentacarbonyl) in a solvent mixture of 1-tetradecene, 1-hexadecene, and 1-octadecene in the presence of oleic acid followed by oxidation with trimethylamine N-oxide. By modulating the boiling point of solvent mixture through the change of its component ratios, the reaction mixture was kept at high temperatures between 270° C. and 300° C. for a reaction time of 1-2 hours. The resulting hydrophobic nanoparticles were first ligand exchanged with 2-[2-(2-methoxyethoxy)ethoxy]acetic acid (MEAA) to ensure their water solubility in a mixture of dimethylformamide (DMF) and water, in which they were further ligand exchanged with dopamine sulfonate (DS) or zwitterionic dopamine sulfonate (ZDS). The dopamine sulfonate (DS) ligand also has a high solubility in water and a strong binding affinity to iron oxide surface, except that the DS is not zwitterionic. Transmission electron microscopy (TEM) images (FIG. 1B-1E) and high-performance liquid chromatography (HPLC, FIG. 3) with size-exclusion column revealed that these nanoparticles have inorganic cores as 7.0, 5.5, 3.0, 2.5 nm, respectively and that the smallest nanoparticles can have a 3.0 nm inorganic core and a 5.0 nm HD. In FIG. 2, it is shown that ZDS-coated nanoparticles can have an $r_2/r_1$ ratio as low as 11 at 7 Tesla (two times lower than the $r_2/r_1$ ratio of commercially available Feraheme™) and 1.5 at 0.5 Tesla (T), which can lead to a high-contrast $T_1$ weighted MR imaging. According to approved Massachusetts Institute of Technology (MIT) institutional protocols, the ZDS-coated nanoparticles were injected into mice and rats, the urine of mice were collected at a series of time points (FIG. 3) and $T_1$ weighted MR images of rats were taken (FIG. 4). A rapid renal clearance of ZDS-coated nanoparticles was observed and the size of the ZDS-coated nanoparticles injected was not affected in vivo (FIG. 3). FIG. 4 also demonstrated that, ZDS-coated nanoparticles injected into rats showed T1 contrast and renal clearance, where the red circle indicates the accumulation of ZDS-coated nanoparticles in urine in the bladder.

Figure 5:
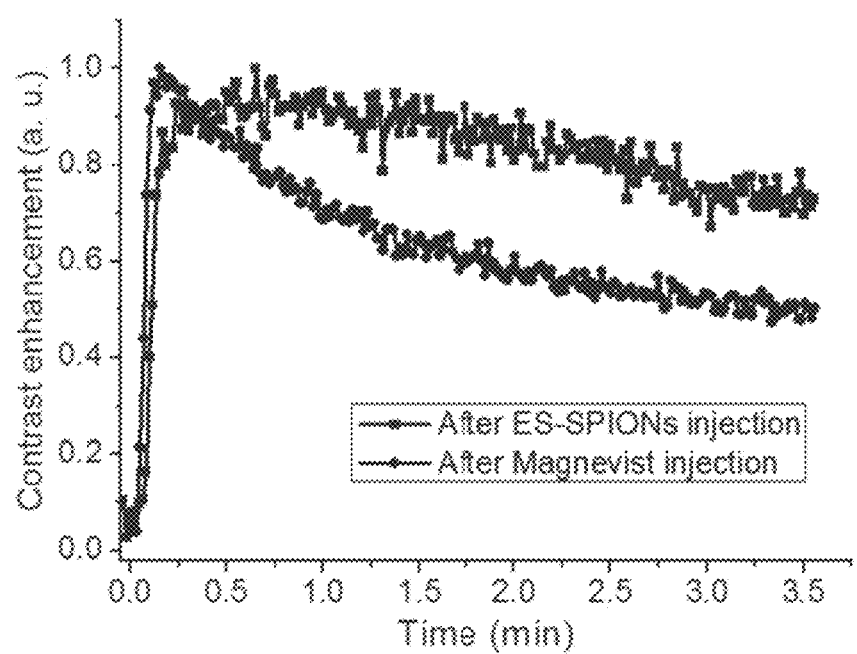
FIG. 5 shows that ES-SPIONs exhibit a significantly longer blood half-life and MRI contrast enhancement compared to Magnevist.
Figure 6:
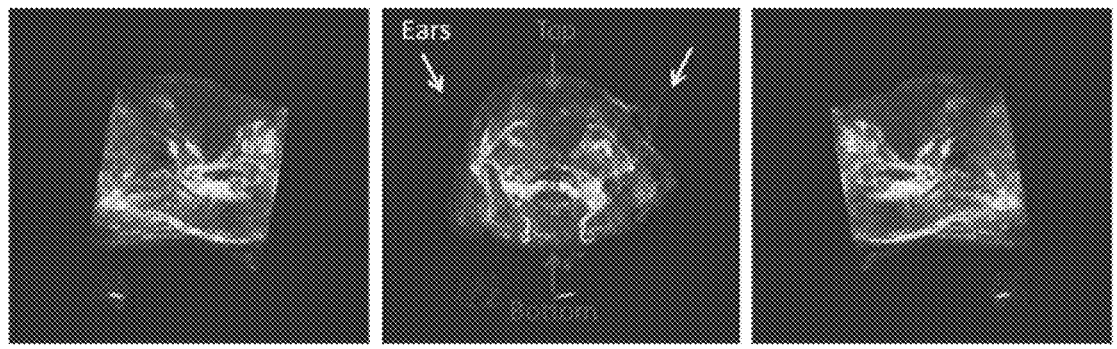
FIG. 6 shows ES-SPIONs are a powerful contrast agent for T1-weighted magnetic resonance angiography at clinical field strength (1.5 T).

The MRI contrast enhancement of Magnevist® (the most commonly used gadolinium-based contrast agents, GBCAs) and ES-SPIONs in blood were compared over time. According to approved animal protocols, mice were scanned in a 1.5 T clinical MRI machine. After intravenous injection of Magnevist or ES-SPIONs, the T1-weighted images of a single slice in mice brain were taken using clinical MRI sequences (~3.5 mins time length), and then the half-life of contrast enhancements of both agents were compared side-by-side. FIG. 5 shows that ES-SPIONs exhibit a significantly longer blood half-life and MRI contrast enhancement compared to Magnevist. As shown in FIG. 5, Magnevist has a half-life of ~2 mins while ES-SPIONs provide constant contrast enhancement for at least ~3.5 mins. This result shows that the ES-SPIONs have a significantly longer blood half-life than that of Magnevist and that the ES-SPIONs offer a more stable MRI contrast enhancement within the length of clinical MRI scan time. Moreover, to demonstrate the capability of ES-SPIONs as blood pool contrast agent for MR angiography (MRA), mice were scanned in a 1.5 T clinical MRI machine, where a T1-weighted 3D MRA sequence was used to image their brain. FIG. 6 shows that ES-SPIONs are a powerful contrast agent for T1-weighted MRA at the clinical field strength (1.5 T). Left and right images show corresponding side views of the image in the middle. It can be seen in FIG. 6 that a three dimensional profile highlighting the blood vessels in brain was generated. The MRA of mice using ES-SPIONs are expected to be enhanced relative to MRA of mice using Magnevist®, because ES-SPIONs provide a more durable contrast enhancement, especially for MRA that lasts longer than 2 mins.

Figure 7:
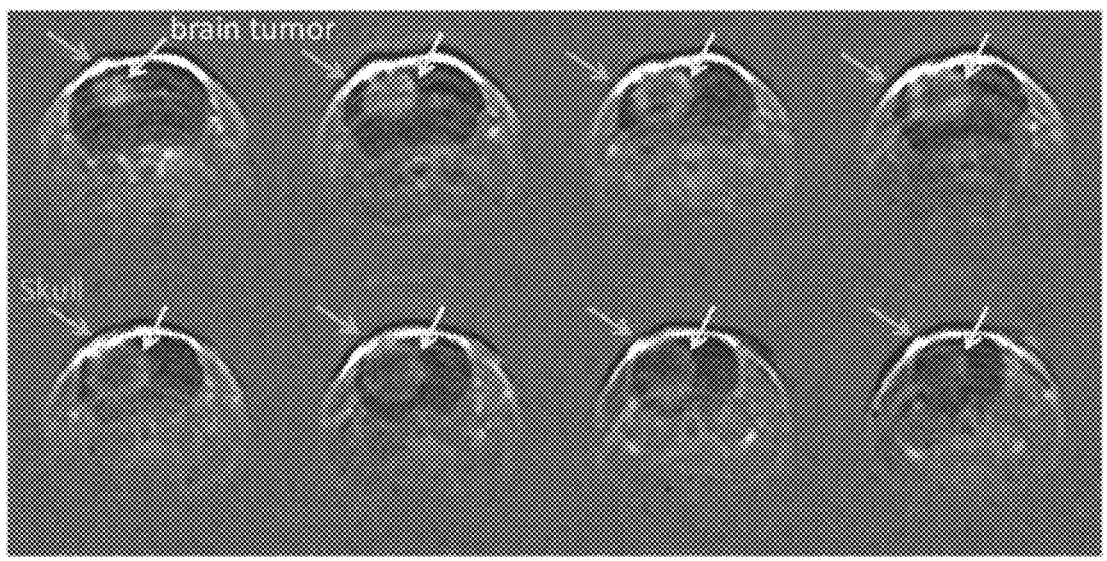
FIG. 7 shows that ES-SPIONs show leakage into advanced brain tumors (U87 glioma model in mice) using T1-weighted MR imaging.

It was also tested whether the ES-SPIONs are able to leak into brain tumors and enhance the MR contrast of brain tumors. A U87 glioma mice model was used, in which the blood-brain-barrier was compromised by their brain tumor. According to approved animal protocols, these mice were scanned in a 9.4 T MRI machine for small animals. A T1-weighted MRI sequence was used to image the mouse head before (pre) and after (post) the intravenous injection of ES-SPIONs and then the pre-images were subtracted from the post images to highlight the contrast enhancement. FIG. 7 shows that ES-SPIONs leak into advanced brain tumors (U87 glioma model in mice) using T1-weighted MR imaging. The images from top left to bottom right show spatially consecutive transversal slices of the head of a mouse. As shown in FIG. 7, ES-SPIONs successfully leak into U87 tumor and then they enhance the T1 contrast of U87 tumor area in the mouse brain. This result suggests that the ES-SPIONs could serve as a non-toxic MRI agent highlighting glioma, which is a major indication where GBCAs are used in the clinic.

Other embodiments are within the scope of the following claims.

What is claimed is:

1. A method for magnetic resonance imaging or magnetic resonance angiography comprising:
    introducing a T1 contrast agent comprising a nanoparticle into a subject, wherein the nanoparticle has an inorganic core of between 2.5 and 4 nm, wherein the nanoparticle has a hydrodynamic diameter of no more than 5 nm, and wherein the nanoparticle is magnetic; and creating an imaging signal of the subject wherein the nanoparticle includes a superparamagnetic iron oxide.

2. The method of claim 1, wherein the inorganic core has a size of between 2.5 and 3.5 nm.

3. The method of claim 2, wherein a surface of the nanoparticle includes a zwitterionic dopamine sulfonate ligand.

4. The method of claim 2, wherein a surface of the nanoparticle includes a DS ligand.

* * * * *